US008202240B2

(12) United States Patent
Felt et al.

(10) Patent No.: US 8,202,240 B2
(45) Date of Patent: Jun. 19, 2012

(54) SYSTEM AND METHOD FOR COLLECTING PLASMA PROTEIN FRACTIONS FROM SEPARATED BLOOD COMPONENTS

(75) Inventors: Thomas J. Felt, Boulder, CO (US); Frank Corbin, III, Littleton, CO (US); Steven Gage Urdahl, Golden, CO (US)

(73) Assignee: CaridianBCT, Inc., Lakewood, CO (US)

( * ) Notice: Subject to any disclaimer, the term of this patent is extended or adjusted under 35 U.S.C. 154(b) by 454 days.

(21) Appl. No.: 12/429,325

(22) Filed: Apr. 24, 2009

(65) Prior Publication Data

US 2010/0042038 A1 Feb. 18, 2010

Related U.S. Application Data

(60) Provisional application No. 61/088,154, filed on Aug. 12, 2008, provisional application No. 61/093,892, filed on Sep. 3, 2008, provisional application No. 60/097,598, filed on Sep. 17, 2008, provisional application No. 61/120,763, filed on Dec. 8, 2008.

(51) Int. Cl.
*A61M 37/00* (2006.01)
*C02F 1/44* (2006.01)

(52) U.S. Cl. ............... 604/6.04; 604/6.09; 604/6.01; 604/6.15; 210/645; 210/500.23

(58) Field of Classification Search ............ 604/4.01, 604/5.01, 6.01, 6.02, 6.04, 6.09, 6.11; 210/645, 210/781, 782, 500.23
See application file for complete search history.

(56) References Cited

U.S. PATENT DOCUMENTS

| | | | |
|---|---|---|---|
| 4,276,140 A | 6/1981 | Jain | |
| 4,350,156 A | 9/1982 | Malchesky et al. | |
| 4,350,594 A | 9/1982 | Kawai et al. | |
| 4,351,710 A | 9/1982 | Jain | |
| 4,609,461 A | 9/1986 | Takata et al. | |
| 4,619,639 A | 10/1986 | Nosé et al. | |
| 4,687,580 A | 8/1987 | Malbrancq et al. | |
| 4,713,176 A | 12/1987 | Schoendorfer et al. | |
| 4,721,564 A | 1/1988 | Harada et al. | |
| 4,728,430 A * | 3/1988 | DiLeo et al. ............ 210/639 |
| 4,746,436 A | 5/1988 | Kopp et al. | |
| 4,776,964 A | 10/1988 | Schoendorfer et al. | |
| 4,780,205 A | 10/1988 | Murakami et al. | |
| 4,789,482 A | 12/1988 | DiLeo et al. | |
| 4,806,247 A | 2/1989 | Schoendorfer et al. | |
| 4,871,462 A | 10/1989 | Fischel et al. | |

(Continued)

FOREIGN PATENT DOCUMENTS

EP 0264931 4/1988

(Continued)

OTHER PUBLICATIONS

International Search Report for PCT/US2009/048134, mailed Jan. 20, 2010.

(Continued)

*Primary Examiner* — Leslie Deak
(74) *Attorney, Agent, or Firm* — Edna M. O'Connor; John R. Merkling; Laura B. Arciniegas (57) ABSTRACT

Method and apparatus for separating plasma from blood in a membrane separator and further separator the separated plasma into desired plasma proteins in a plasma separator fluidly connected to the membrane separator to receive the separated plasma.

22 Claims, 5 Drawing Sheets

U.S. PATENT DOCUMENTS

| | | | |
|---|---|---|---|
| 4,911,833 A | 3/1990 | Schoendorfer et al. | |
| 4,985,153 A | 1/1991 | Kuroda et al. | |
| 5,008,012 A | 4/1991 | Hagihara et al. | |
| 5,141,490 A | 8/1992 | Fujii et al. | |
| 5,217,618 A | 6/1993 | Murakoshi | |
| 5,358,482 A | 10/1994 | Panzani | |
| 5,460,715 A * | 10/1995 | Kawamura et al. | 210/97 |
| 5,516,431 A | 5/1996 | Kawamura et al. | |
| 5,871,649 A | 2/1999 | Ofsthun et al. | |
| 5,954,971 A | 9/1999 | Pages et al. | |
| 6,669,905 B1 | 12/2003 | Mathias et al. | |
| 7,025,881 B2 | 4/2006 | Heim | |
| 7,267,771 B2 | 9/2007 | Gorsuch et al. | |
| 7,470,245 B2 | 12/2008 | Tu et al. | |
| 7,481,936 B2 | 1/2009 | Gorsuch et al. | |
| 7,563,376 B2 | 7/2009 | Oishi | |
| 2002/0033370 A1 | 3/2002 | Bainbridge et al. | |
| 2002/0062100 A1 * | 5/2002 | Pierce et al. | 604/6.01 |
| 2002/0099174 A1 | 7/2002 | Johnston et al. | |
| 2004/0182787 A1 | 9/2004 | Chevallet et al. | |
| 2006/0129082 A1 | 6/2006 | Rozga | |
| 2006/0186044 A1 | 8/2006 | Nalesso | |
| 2006/0226090 A1 | 10/2006 | Robinson et al. | |
| 2006/0287628 A1 * | 12/2006 | Hirabuki | 604/6.01 |
| 2007/0034579 A1 | 2/2007 | Dorian et al. | |
| 2008/0135502 A1 | 6/2008 | Pyo et al. | |

FOREIGN PATENT DOCUMENTS

| | | |
|---|---|---|
| KR | 2008/0052036 | 6/2008 |
| WO | WO01/58496 | 8/2001 |

OTHER PUBLICATIONS

International Search Report for PCT/US2009/048087, mailed Feb. 3, 2010.

* cited by examiner

SYSTEM AND METHOD FOR COLLECTING PLASMA PROTEIN FRACTIONS FROM SEPARATED BLOOD COMPONENTS

CROSS REFERENCE TO RELATED APPLICATIONS

This application claims benefit under 35 U.S.C. 119(e) of U.S. Provisional Application Nos. 61/088,154 filed Aug. 12, 2008; 61/093,892, filed Sep. 3, 2008, 61/097,598, filed Sep. 17, 2008 and 61/120,763, filed Dec. 8, 2008.

This application is related to U.S. Ser. No. 12/429,266 filed on Apr. 24, 2009.

BACKGROUND

For transfusions of blood and blood components, whole blood from a single donor is typically separated into three components: plasma, red blood cells and platelets. Each component may be used to treat a multiplicity of specific conditions and disease states. For example, the red blood cell component may be used to treat anemia and replace red blood cell loss due to bleeding, the concentrated platelet component may be used to control bleeding, and the plasma component may be given to patients to increase blood volume, or may be separated off-line after collection into individual plasma proteins such as fibrinogen, von Willebrand factor, Factor VIII, Factor IX, Anti-thrombin III, Fibrin sealant, thrombin, Alpha I and IVIG. Plasma from multiple donors may also be collected and combined or pooled together, and the combined plasma pool fractionated into the desired plasma proteins.

The separation of the collected plasma component into various protein or plasma components or fractions is called plasma fractionation. Such fractionation is typically done by large scale fractionators which combine plasma from many donors and concentrate individual plasma proteins by using the known techniques of cold alcohol fractionation (also known as Cohn fractionation) and chromatography.

There are traditionally two ways to obtain separated blood components from single donors. One way is to collect whole blood from donors and separate it into components at some time period after the whole blood collection. Using this method, whole blood is collected into approved containers that are pyrogen-free and sterile, and contain sufficient anticoagulant for the quantity of blood to be collected. The whole blood is then separated into components in a lab by a technician, and separation typically occurs from between about 2 and 8 hours after collection in the United States, and between about 2 to 24 hours in Europe.

Another way to separate whole blood into components is by using an apheresis device. These apheresis devices separate whole blood from a single donor, connected on-line to the device, into components automatically, and return any uncollected and unneeded blood components back to the donor during the collection procedure.

Apheresis devices may be used to separate the plasma component from the cellular components of a blood donation. Apheresis devices permit more frequent donations by a single donor due to the return of uncollected components.

BRIEF SUMMARY OF THE INVENTION

One embodiment of the invention relates to an integrated pre-connected disposable set for separating whole blood into plasma protein fractions comprising a first membrane separator for separating whole blood into plasma and other blood components, a plasma collect tubing pre-connected to a first outlet of the first membrane separator, a second membrane separator comprising an inlet pre-connected to the plasma collect tubing and a first outlet fluidly connected to a plasma protein collection container wherein separated plasma exiting the first membrane separator passes through the collect tubing to the second membrane separator for separation into desired plasma proteins and wherein such plasma proteins are collected in the plasma protein collection container.

Also included in the invention is an apparatus for separating whole blood into plasma proteins comprising a pump system for cooperating with an integrated pre-connected disposable set comprising a removal pump for removing blood from a donor, a return pump for returning uncollected blood components to the donor, a collect pump for pumping separated plasma to a plasma separator. The integrated pre-connected set comprises a first membrane separator for receiving blood removed by the removal pump and separating such blood into plasma and other blood components, a second membrane separator for receiving separated plasma pumped by the collect pump from the first membrane separator and for separating such plasma into at least one plasma protein fraction, and a collection bag fluidly connected to the second membrane separator for receiving the at least one plasma protein fraction.

A further aspect of the invention relates to a method of collecting a concentrated plasma product from whole blood by removing whole blood from a donor; separating the whole blood using a first membrane separator into a plasma component and other components; returning the other components to the donor; separating the separated plasma using a second membrane separator into at least one protein fraction; and collecting the separated at least one protein fraction.

DETAILED DESCRIPTION

It should be noted that like elements are represented using like numerals. This invention is described with reference to a plasma separation system having two membrane separators, one for separating plasma from whole blood and the other for separating desired plasma proteins from the plasma. The system shown is for continuously separating plasma as a blood component from a donor and returning uncollected blood components back to the donor.

The invention may be used with the apheresis systems of other manufacturers such as the Autopheresis C system manufactured by Fenwal, Inc. Lake Zurich, Ill., U.S.A. or the PCS system as manufactured by Haemonetics Corp. of Bainbridge, Mass., U.S.A.

Figure 1:
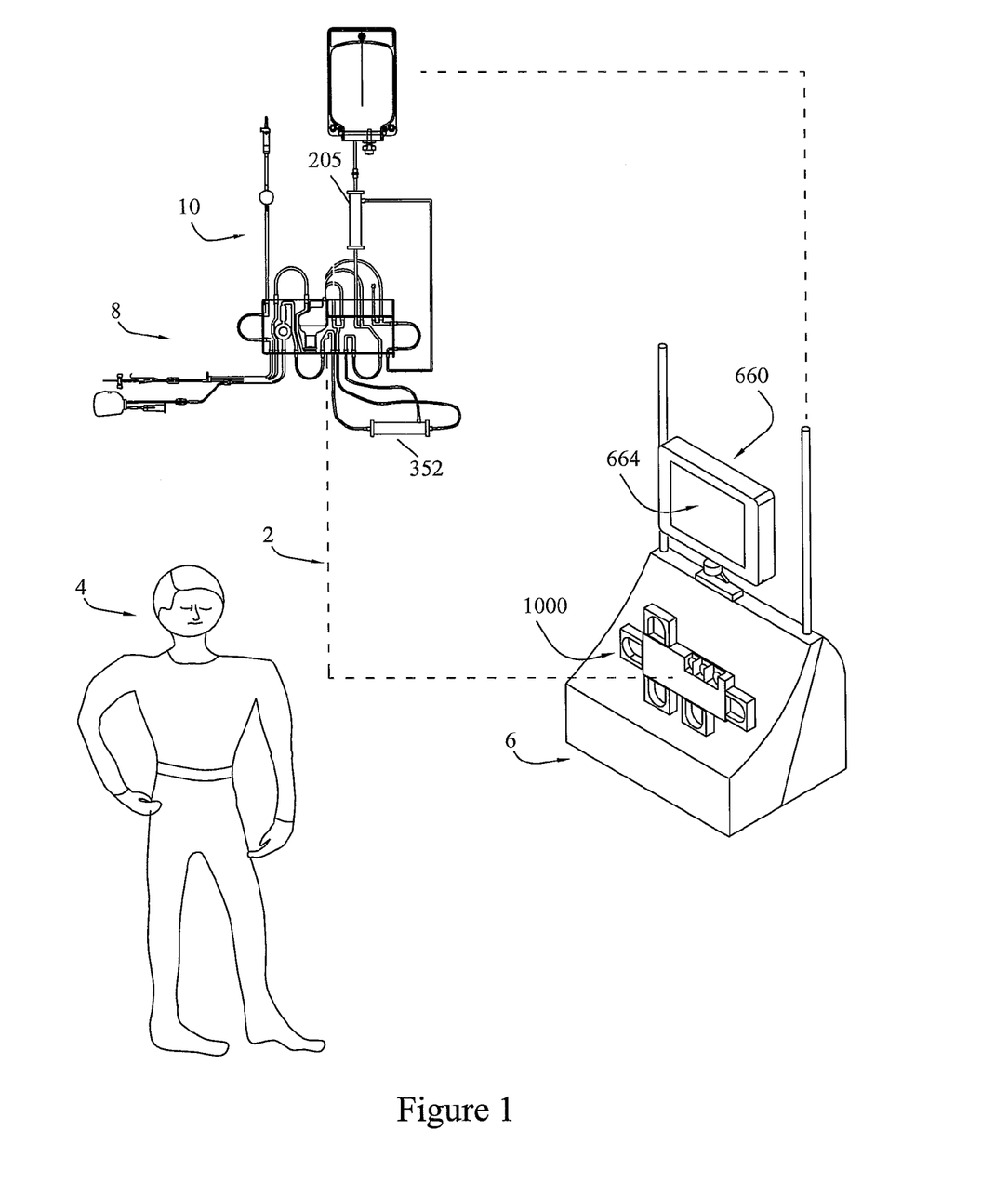
FIG. 1 is a schematic view of a system for separating plasma from other blood components and for further separating the plasma into plasma proteins.

A blood apheresis system 2 is illustrated in FIG. 1 and allows for a continuous blood component separation process. Generally, in a continuous system, whole blood is withdrawn from a donor/patient 4 and provided to a blood component separation device 6 where the blood is separated into the individual blood components with at least one of these blood components being removed from the device 6 with the other components being returned to the donor. The continuous system 2 also provides for further separation or concentration of plasma into plasma proteins for collection.

In the blood apheresis system 2, blood is withdrawn from the donor/patient 4 and directed through a pre-connected disposable set 8 which includes an extracorporeal tubing circuit 10, membrane separator or filter 352 and a plasma separator or concentrator 205 which defines a completely closed and sterile system. The disposable set 8 can be for single use and to facilitate such is mounted on a separation device 6 which includes a pump/valve/sensor assembly 1000 for interfacing with the extracorporeal tubing circuit 10.

The blood within the membrane separator 352 is separated into two blood component types, one of which is plasma, which may be continually removed from the membrane separator 352. The plasma component may then be further concentrated or separated into plasma proteins. Components, other than the plasma for further separation, flow from the membrane separator 352 to be returned to the donor/patient 4 via the extracorporeal tubing circuit 10.

Operation of the blood component separation device 6 is controlled by one or more processors, not shown. In order to assist the operator of the separation system 2 with various aspects of its operation, the blood component separation device 6 may include a graphical interface 660 with a touch screen input/output device 664.

The pre-connected disposable tubing circuit will be described with respect to a fluid flow cassette assembly as such cassette assembly permits ease of loading the disposable set or circuit with respect to any pumps. However, such cassette is optional.

Figure 2:
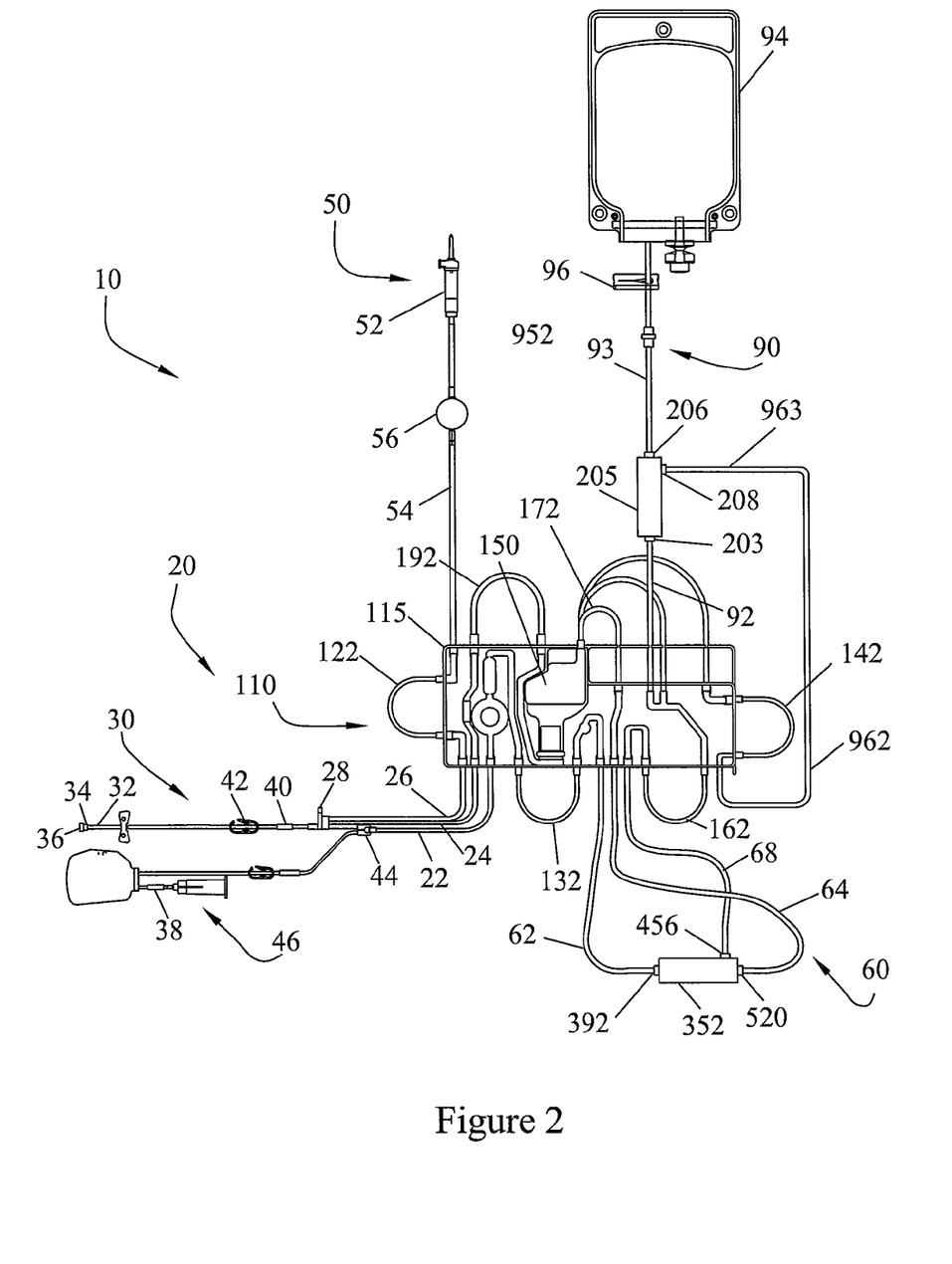
FIG. 2 is a schematic view of the closed sterile disposable of FIG. 1.

As illustrated in FIG. 2, blood-primable pre-connected extracorporeal tubing circuit 10 comprises a cassette assembly 110 and a number of tubing assemblies 20, 50, 60, and 90. Generally, blood removal/return tubing assembly 20 provides a single needle interface between a donor/patient 4 and cassette assembly 110, and blood inlet/blood component tubing subassembly 60 provides the interface between cassette assembly 110 and membrane separator 352. An anticoagulant tubing assembly 50, and plasma or plasma protein collection tubing assembly 90 are also interconnected with cassette assembly 110. The extracorporeal tubing circuit 10, including the assemblies or sub-assemblies above, and membrane separator 352 are interconnected to yield a closed disposable system or pre-connected disposable for a single use.

The blood removal/return tubing assembly 20 includes a needle subassembly 30 interconnected with blood removal tubing 22, blood return tubing 24 and anticoagulant tubing 26 via a common manifold 28. The needle subassembly 30 includes a needle 32 having a protective needle sleeve 34 and needle cap 36, and interconnect tubing 38 between needle 32 and manifold 28. Needle subassembly 30 further includes a D sleeve 40 and tubing clamp 42 positioned about the interconnect tubing 38. Blood removal tubing 22 may be provided with a Y-connector 44 interconnected with a blood sampling subassembly 46.

Cassette assembly 110 includes front and back molded plastic plates (not shown) that are hot-welded together to define a rectangular cassette member 115 having integral fluid passageways. The cassette assembly 110 further includes a number of outwardly extending tubing loops, described below, interconnecting various integral passageways. The integral passageways are also interconnected to the various tubing assemblies.

The blood removal/return assembly includes first integral passageway 190a connected to the bottom of reservoir 150, tubing loop 192 and second integral fluid passageway interconnected with tubing loop 192 and blood return tubing 24.

Figure 3:
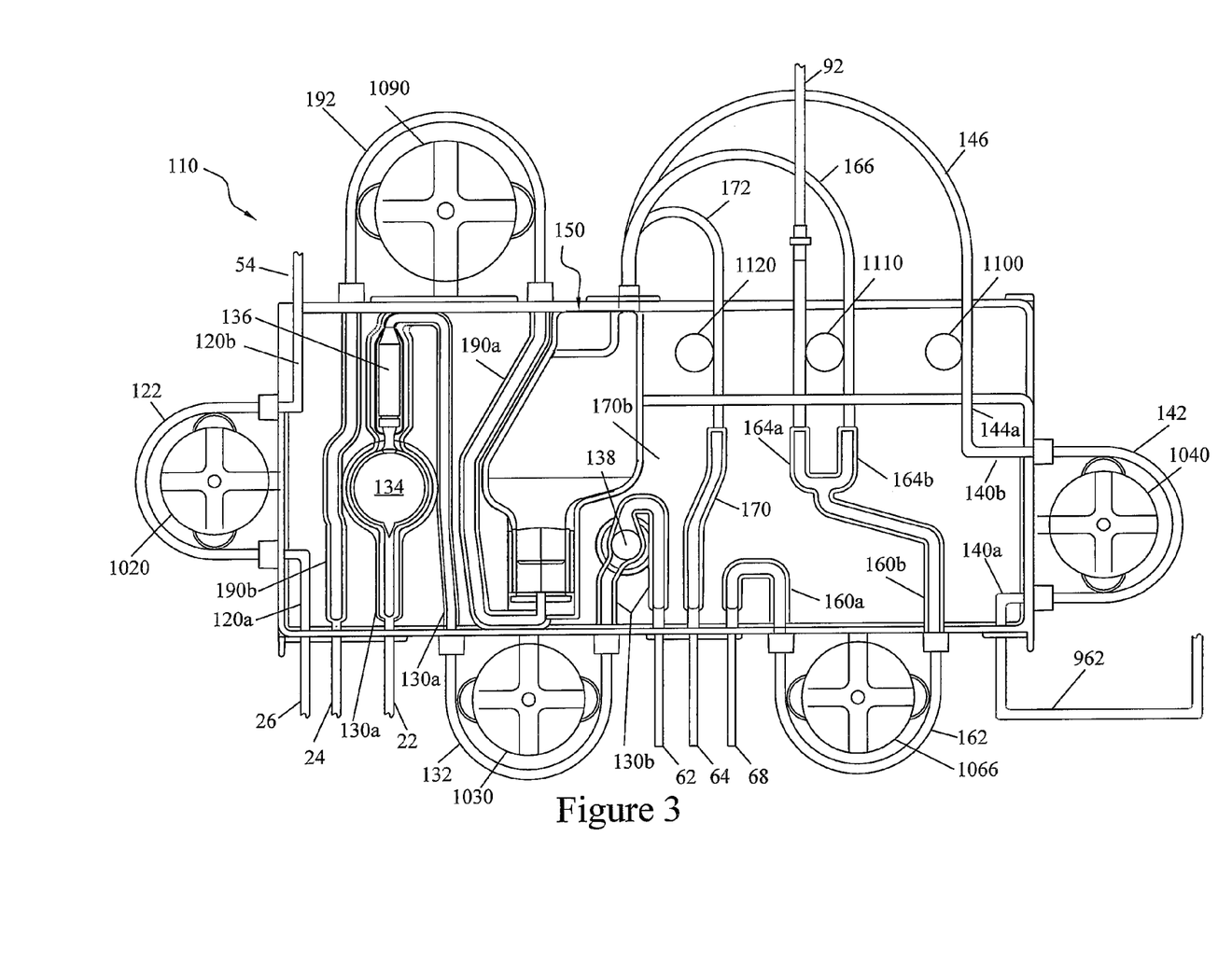
FIG. 3 is a schematic view of a detail of the disposable of FIG. 2.

As seen in FIG. 3, cassette assembly 110 includes a first integral anticoagulant passageway 120a interconnected with the anticoagulant tubing 26 of the blood removal/return tubing assembly 20. The cassette assembly 110 further includes a second integral anticoagulant passageway 120b and a pump-engaging, anticoagulant tubing loop 122 between the first and second integral anticoagulant passageways 120a, 120b. The second integral anticoagulant passageway 120b is interconnected with anticoagulant tubing assembly 50. The anticoagulant tubing assembly 50 includes a spike drip chamber 52, (FIG. 2) connectable to an anticoagulant source, anticoagulant feed tubing 54 and a sterile barrier filter 56. During use, the anticoagulant tubing assembly 50 supplies anticoagulant to the blood removed from a donor/patient 4 to reduce or prevent any clotting in the extracorporeal tubing circuit 10.

Cassette assembly 110 also includes a first integral blood inlet passageway 130a interconnected with blood removal tubing 22 of the blood removal/return tubing assembly 20. The cassette assembly 110 further includes a second integral blood inlet passageway 130b and a pump-engaging, blood inlet tubing loop 132 between the first and second integral blood inlet passageways 130a, 130b. The first integral blood inlet passageway 130a includes a first pressure-sensing module 134 and inlet filter 136, and the second integral blood inlet passageway 130b includes a second pressure-sensing module 138. The second integral blood inlet passageway 130b is interconnected with blood inlet tubing 62 of the blood inlet/blood component tubing assembly 60.

Blood inlet tubing 62 is also interconnected with inlet port 392 of membrane separator 352 to provide whole blood thereto for processing or separation. To return separated blood components to cassette assembly 110 for return to the donor, the blood component tubing assembly 60 further includes an outlet tubing 64 connected with outlet port 520. The blood inlet/blood component tubing assembly 60 also includes plasma outlet tubing 68 connected to outlet port 456.

The plasma outlet tubing 68 of blood inlet/blood component tubing assembly 60 interconnects with a first integral plasma passageway 160a of cassette assembly 110. Cassette assembly 110 further includes a pump-engaging, plasma tubing loop 162 interconnecting the first integral plasma passageway 160a and a second integral plasma passageway 160b. The second integral plasma passageway 160b includes first and second spurs 164a and 164b. The first spur 164a is interconnected to the plasma collection tubing assembly 90. The plasma collection tubing assembly 90 may be employed to collect plasma during use and includes plasma collector tubing 92, concentrator or separator 205, plasma collector tubing 93 and one or more plasma collection bags, containers or reservoir 94. A slide clamp 96 may be provided on plasma collector tubing 93. The plasma collection tubing assembly 90 may also be employed for further separation of the plasma component as will be described in more detail below.

The second spur 164b of the second integral plasma passageway 160b is interconnected to a plasma return tubing loop 166 to return plasma to donor/patient 4. For such purpose, the plasma return tubing loop 166 is interconnected to the top of the blood return reservoir 150 of the cassette assembly 110.

The plasma return assembly may also return plasma after separation or concentration. The post separation return includes tubing 963 which connects to tubing 962 (optionally this can be continuous tubing), spurs 140a and 140b as well as pumps engaging plasma tubing loop 142. Spur 144a is connected to plasma return loop or tubing 146 to deliver plasma to cassette reservoir 150 for ultimate delivery to the donor/patient 4.

Although the plasma return assembly is shown returning plasma through tubing loop 142, the plasma could also be returned through another pump loop arrangement such as 162.

The plasma collection tubing assembly further includes a plasma separation sub-assembly shown in FIG. 2 including a second membrane separator or hollow fiber membrane separator or concentrator 205. Tubing 92 is interconnected to the inlet 203 of the separator 205. Tubing 93 is interconnected to the outlet 206 of the membrane separator 205. Plasma collection tubing assembly 90 also includes tubing 963, interconnected to second outlet 208 for returning plasma or proteins that are not to be collected. The plasma return assembly including return tubing 963 connects to tubing 962 and spur 140a as described above.

Figure 4:
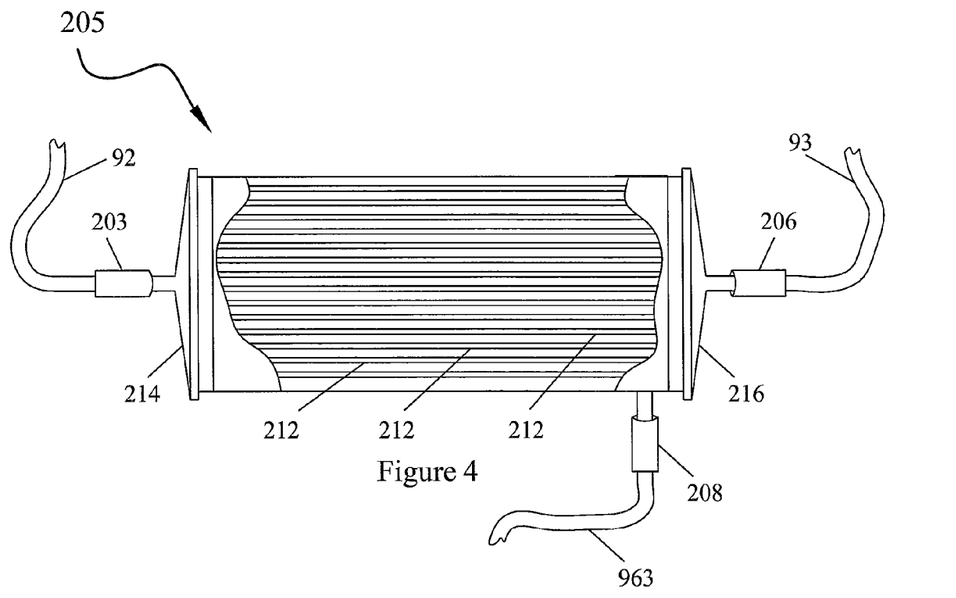
FIG. 4 is a schematic view of the plasma separator of the disposable of FIG. 2.

The plasma separator 205 includes inlet 203 in first end cap 214 and outlet 206 in the opposite end cap 216.

Hollow fibers are arranged between the two end caps 214 and 216. Such hollow fibers 212 include inter-capillary space (IC) within the fiber and an extra-capillary space (EC) outside the hollow fibers. The pore size of the membrane formed from the hollow fibers may be selected so that components such as plasma or optionally, protein of selected molecular weight may pass between the IC and EC spaces. Thus, if separated plasma from the first membrane separator 352 enters through tubing 92 and inlet 203 into the IC space, plasma and any proteins able to pass through the membrane pores to the EC space will pass through outlet 208 and tubing 963.

Table 1 below shows various protein factions and their molecular weight in kilodalton. The pore size of the membrane can be chosen to have a cut off value to pass through the membrane all but the desired protein fractions such as those given in the table. For example, the pore size could be such to pass all below 50 kilodaltons or the pore size could be selected to pass through the membrane those in a range in which the cut off value is selected between 50 kDa and 1300 kDa.

TABLE 1

| Constituent | Molecular Weight (kDa) |
| --- | --- |
| Cholesterol | 1,300 |
| IgM | 950 |
| Fibrinogen | 340 |
| Factor VIII | 100-340 |
| IgE | 190 |
| IgD | 175 |
| IgA | 160 |
| IgG | 150 |
| Haptogloblin | 100 |
| Albumin | 66 |
| A1Antitrysin | 54 |
| Factor VII | 50 |

For example, a membrane having a pore size such that only constituents with a molecular weight of less than 50 kDa will pass, all proteins in Table 1 will be collected through outlet 206 with only plasma less proteins being returned through outlet 208.

By further example, for a membrane having a pore size such that only constituents having a molecular weight of less than 150 kDa will be returned, only a portion of the proteins with a molecular weight greater than 150 kDa will be collected. Plasma and other plasma proteins of less than 150 kDa molecular weight will pass through the membrane to outlet 208.

The return outlet tubing 64 from first membrane separator 352 for other blood components of the blood inlet/blood component tubing assembly 60 is interconnected with integral passageway 170 of cassette assembly 110 (FIG. 3). The integral other component return passageway 170 includes first spur 170a. The first spur 170a is interconnected with return tubing loop 172 to return separated other blood components to a donor/patient 4. For such purpose, the return tubing loop 172 is interconnected to the top of blood return reservoir 150 of the cassette assembly 110.

As illustrated in FIG. 3, pump-engaging tubing loops 122, 132, 142, 162 and 192 extend from cassette member 115 to yield an asymmetric arrangement thereby facilitating proper mounting of cassette assembly 110 on blood component separation device 6 for use.

In normal operation, whole blood will pass through needle assembly 30, blood removal tubing 22, cassette assembly 110 and blood inlet tubing 62 to membrane separator 352. The whole blood will then be separated into plasma and other blood components in separator 352. During product collection, only plasma will be passed out of separator 352 through port 456 for collection and further separation.

In the cassette assembly a reservoir 150 having upper and lower ultrasonic sensors (not shown) is also provided such that, during the blood processing mode, return blood will be removed from reservoir 150 during each blood return/replacement delivery sub-mode and accumulated during each blood removal sub-mode. When uncollected platelets, red cells and potentially white blood cells from membrane separator 352 have accumulated in reservoir 150 up to upper ultrasonic level sensor (not shown), operation of the pump 1090 associated with pump loop 192 will be initiated to remove the blood or replacement components from reservoir 150 and transfer the same back to the donor/patient 4 via the return/delivery tubing 24 and needle assembly 20. When the fluid level in the reservoir 150 drops down to the level of the lower ultrasonic level sensor, the return/delivery peristaltic pump 1090 will automatically turn off reinitiating blood removal sub-mode. The cycle between blood removal and blood return/replacement delivery sub-modes will then continue until a predetermined amount of plasma proteins have been collected.

Reservoir 150 may also have a gas vent (not shown) to a gas bag so that, during priming, air may be evacuated from the system.

Pump 1040 is associated with tubing pump loop 142, pump 1066 is associated with tubing loop 162, pump 1030 is associated with tubing loop 132, pump 1020 is associated with tubing loop 122, and pump 1090 is associated with tubing loop 192 when the cassette 110 is mounted on pump/valve/sensor assembly 1000.

The first membrane separator 352 includes a hollow fiber membrane arranged between end caps similar to that described for the plasma separator 205. However, it has a selected pore size such that only plasma including plasma proteins will pass through the membrane from inlet 392 to outlet port 456. Larger molecular weight components such as blood cells will continue to flow through the IC portion from inlet 392 to outlet port 520 for return to the donor.

As shown in FIG. 2, blood is introduced into the interior of the membrane separator 352 through a blood inlet port 392 from inlet tubing 62. The blood inlet port 392 is in one end cap of the membrane separator such that the blood may pass into IC space of separator 352.

Due to the pore size of the membrane, constituents or components such as plasma or plasma proteins will pass through the membrane to separate the plasma from the other components.

Separated plasma exits the blood processing vessel through port 456 and tubing 68. All other components exit the blood through port 520 and tubing 64.

The separation system includes various valve assemblies shown schematically at 1120, 1110, and 1100 in FIG. 3. These valve assemblies form part of the pump/valve/sensor assembly and cooperate with the disposable system 10.

The system described herein provides for continuous separation of plasma with a continuous plasma separation or concentration step. The non-collected components are re-infused back to the donor.

The initiation of blood processing provides for the collection of plasma in one or more reservoir(s) 94. During the collection procedure, blood component separation device 6 preferably controls the initiation and termination of successive blood removal and blood return. Additionally, blood component separation device 6 will control the plasma collection processes according to predetermined protocols, preferably including control over the valve assemblies 1100, 1110 and 1120 of the pump/valve/sensor assembly 1000, and/or the appropriate pumps 1020, 1030, 1040, 1066 and/or 1090.

Initially, priming with saline is carried out to prime the disposable system 10.

After priming is completed, yet still during the set-up phase, blood component separation device 6 may provide appropriate control signals to the pump/valve/sensor assembly 1000 such that all separated blood components flowing out of membrane separator 352 will first pass to return/delivery reservoir 150. Optionally, one or more cycles of separation and return of all blood components back to the donor may be performed before collection. Also, blood component separation device 6 may continue operation of blood inlet pump assembly 1030 associated with pump loop 132 during one or more these initial blood component return sub-modes.

To establish the desired AC ratio, blood component separation device 6 provides appropriate control signals to anticoagulant peristaltic pump 1020 so as to introduce anticoagulant into the blood inlet flow at a predetermined rate. The inlet flow rate of anti-coagulated blood to blood processing vessel 352 may be limited by a predetermined, maximum acceptable anticoagulant infusion rate (ACIR) to the donor/patient 4.

When collection begins, blood component separation device 6 may provide control signals so that plasma divert valve assembly 1110 switches to divert the flow of separated plasma pumped from membrane separator 352 through plasma outlet tubing 68 and plasma tubing loop 162 into plasma collector tubing 92 through inlet 203 of second membrane separator 205. See also FIG. 5 which shows a simplified view of the system. Other components will continue to flow from membrane separator 352 through outlet tubing 64 through return tubing loop 172 into blood return reservoir 150.

During the collection processes, one or more replacement fluid(s) may optionally be delivered to the donor/patient 4. Thus, whenever the separation device 6 is in a collection rather than the return mode, replacement fluid (not shown) may be introduced, for example, through tubing line 962, cassette passageways 140a and 140b, and tubing loops 142 and 146 into the reservoir 150 or may otherwise be aspirated into the system.

Figure 5:
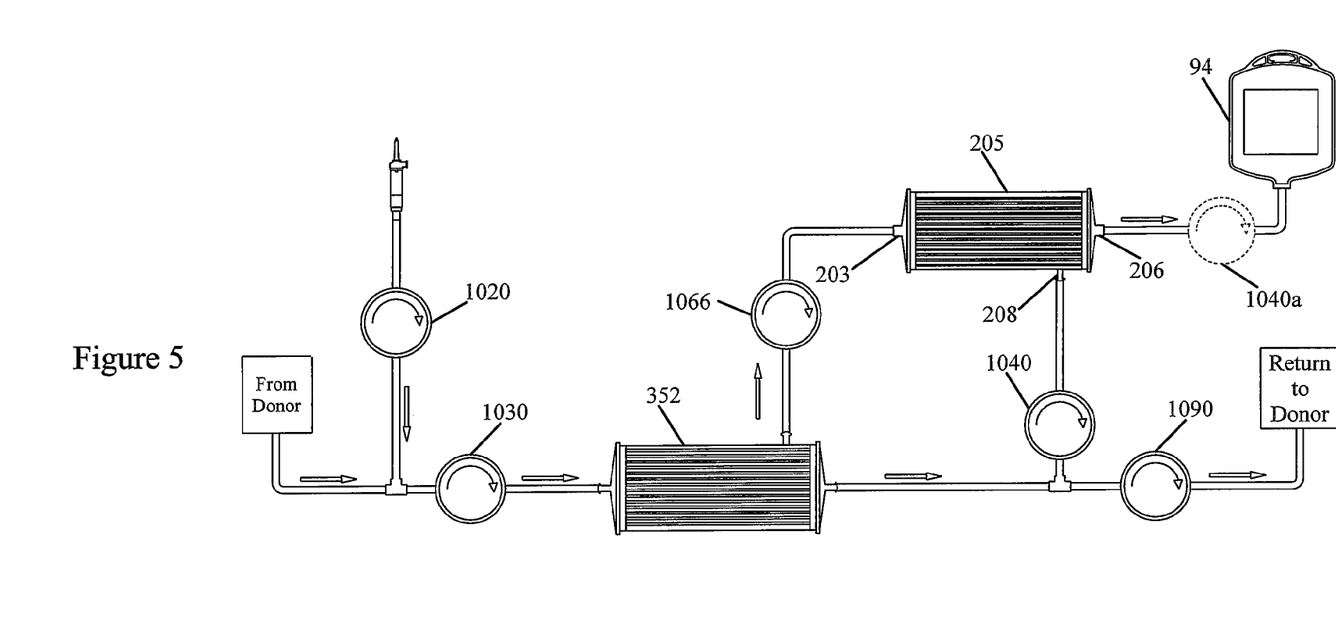
FIG. 5 is a schematic view of the system of FIG. 1 with detail removed.

With respect to plasma collection, the separated plasma from membrane separator 352 is pumped via pump 1066 through the plasma collect line 92 through filter, separator or concentrator 205 to plasma component collection bag 94 through line 93.

The separated plasma is pumped out of membrane separator 352 through port 456, line 68, passageway 160a, tubing 162, passageway 160b, 164a, by pump 1066 around which tubing 162 extends and flows via plasma collect line 92 into separator 205. The fraction of plasma proteins that do not pass through the filter membrane in the membrane separator 205 from the IC to the EC flow into storage bag 94. The remainder of the plasma and/or proteins that pass to the EC side flow out of the filter 205 through outlet 208, tubing 963, 962, passageway 140a, tubing loop 142, passageway 140b, tubing 146, to reservoir 150 and back to the donor 4. An enriched plasma product, which may contain several times the normal amount or an increased concentration of the desired protein, could be produced by simply processing more plasma through the filter, concentrator or separator 205.

Following collection of the desired quantity of plasma protein and after blood separation device 6 has provided control signals to divert assemblies 1110 and 1120, so as to divert the respective separated plasma and separated other component flows to reservoir 150, if further blood processing is not desired, rinse back procedures may then be completed. The plasma pump 1066 is set at the full plasma rate equal to rate of the return/delivery pump 1090 for rinse back.

At the end of the procedures, the plasma bag(s) 94 may be disconnected from the extracorporeal tubing circuit 10.

The pore size of the membrane 212 in the separator 205 determines whether all proteins are collected in container 94 or only those proteins of sufficiently high molecular weight.

The simplified FIG. 5 also indicates another option. As shown in FIG. 5 the plasma entering the plasma separator 205 is pumped on the inlet side 203 by pump 1066 and also the outlet (EC) side 208 by pump 1040. However the locations of the pumps can be varied. For example, as shown in FIG. 5 there also may be a pump on the IC exit side, (illustrated in phantom lines as 1040a). This pump may be used with the inlet pump 1066 alone, (no pumping through 1040 on the EC side) or it may be used with pump 1040 alone, (no pumping through 1066 into the inlet or IC side). Thus two pumps are utilized but the exact locations of such pumps may be varied.

Having pump 1040a pump on the IC side from 206 provides flow through the membrane by positive pressure on the IC side thus avoiding any degassing of the fluid as may occur using pumps 1066 and 1040 which exerts negative pressure on the EC side. If the membrane 212 becomes blocked when pump 1040a is used the compression force of the rollers of pump 1040a could be such that they will lift sufficiently and provide less occlusion for the over volume or pressure. Thus it can function as a pressure relief valve.

This continuous procedure permits desirable proteins to be collected and removed from a donor with the remainder of the plasma proteins and other blood components being returned to the donor. This enables maximum collection and concentration of the desired proteins, instead of the smaller amount of desired protein contained within a single blood donation.

Using this procedure, desired plasma proteins may be collected from a donor, while the undesired components may be returned to the donor. This would enable greater amounts of desired plasma proteins to be collected from a single donor, without increasing the risk to the donor as the amount of fluid volume removed from a donor would not be detrimental. More plasma can be processed resulting in the collection of increased amounts of plasma protein. However, from the donor perspective the increased collection of proteins can be collected with the same volume removal as a typical plasma collection.

The final concentration of the protein-enriched product could be adjusted by adjusting the ratio of the plasma flow into the filter and the plasma flow out of the filter. This can be done by adjusting pump speed of pump 1066, 1040 or 1040a. For example, if the membrane excluded all proteins and the flow rate through the filter was half that of the plasma flow into the filter, the resultant concentration of the proteins would be double that of normal donor plasma.

If it is desired to collect high molecular weight proteins, the filter/column 205 could separate on a continuous basis the albumin and other low molecular weight proteins and return them to the donor, while collecting higher molecular weight fractions such as fibrinogen, IgG, von Willebrand factor and factor VIII.

Figure 6:
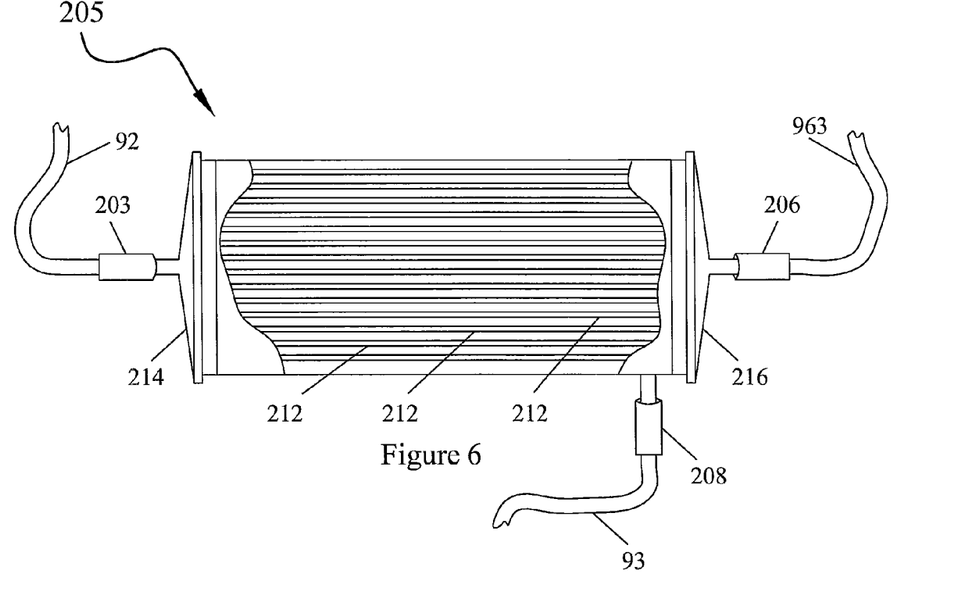
FIG. 6 is a schematic view of a variation of the plasma separator of FIG. 4.

An alternative arrangement for the filter concentrator could also be provided as shown in FIG. 6. If lower molecular weight proteins are desired, the higher molecular weight proteins could be returned to the donor, while the lower molecular weight proteins are collected by changing the tubing so that those that pass through the membrane are collected rather than returned. In this configuration outlet 208 would be connected to tubing 93 with outlet 206 being connected to tubing 963 for return to the donor.

Also, although the above is described with respect to the separated plasma entering the IC side of the membrane, such plasma could enter the EC side with the low molecular constituents passing to the IC side through the membrane. Collection would be through port 206 if low molecular fractions are desired or through port 208 if higher molecular weight fractions are collected.

As described above, such separation specificity can be accomplished by selecting membranes which have pore sizes which correspond to the molecular weight of the desired protein.

The high concentration protein collected could be used to enrich the plasma of a patient for therapeutic purposes. The high-concentration product may also be used for additional fractionation as described below where its yield of proteins would be much higher compared to normal plasma and thus produce an increased amount of protein concentrate products.

Figure 7:
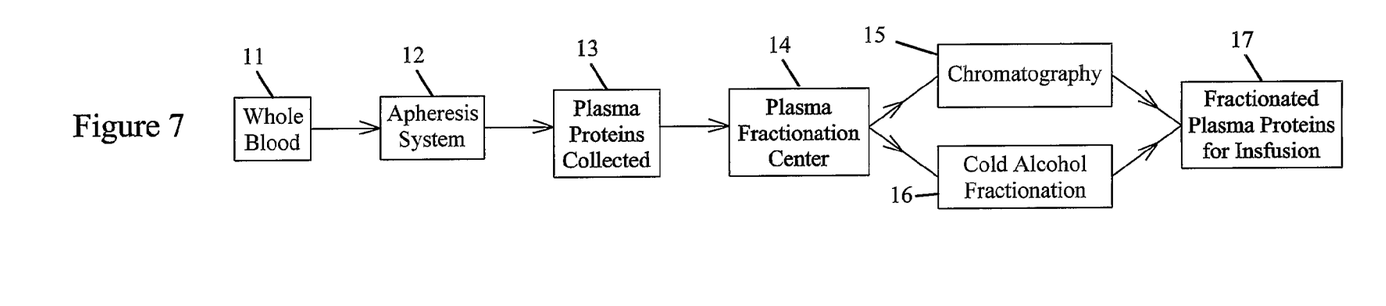
FIG. 7 is a block diagram illustrating a process using collected apheresis plasma proteins for further fractionation.

FIG. 7 illustrates, in block diagram form, the process of taking whole blood from a donor, (whole blood 11), and using apheresis apparatus 12 as described above to collect a concentrated plasma protein fraction 13. The plasma proteins 13 from the apheresis process may optionally be provided to plasma fractionation center 14, and optionally pooled with other collections, for further fractionation or concentration of such product utilizing a known plasma fractionation process such as cold alcohol fractionation 16 (also known as Cohn fractionation) or chromatography 15. Other known fractionation processes could be used. This process could be used to provide a highly concentrated plasma protein infusion product 17 such as IVIG or clotting factor. Cold alcohol fractionation includes the addition of alcohol to the collected apheresis protein product while simultaneously cooling the protein product. This causes the selected plasma proteins to precipitate out of any remaining plasma or other non-selected proteins. Chromatography includes the method of passing the apheresis plasma proteins through a stationary phase to separate out further the desired proteins from other proteins and any remaining plasma. These processes result in a further concentrated product of the desired proteins. Such product may be frozen until needed as an infusion product.

The above has been described with respect to a fluid flow cassette having internal passageways. It is understood that other fluid flow arrangements instead of the specific internal passageway cassette could be used.

It will be apparent to those skilled in the art that various modifications and variations to the methods and structure of the present invention can be made without departing from its scope. Thus it should be understood that the invention is not be limited to the specific examples given. Rather, the invention is intended to cover modifications and variations provided they come within the scope of the following claims and their equivalents.

The invention claimed is:

1. An integrated pre-connected disposable set for separating whole blood into plasma protein fractions comprising:
    a first hollow fiber membrane separator having an inlet and a first outlet for separating whole blood into plasma and other blood components;
    a plasma collect tubing pre-connected to the first outlet of the first membrane separator;
    a plasma protein collection container; and
    a second hollow fiber membrane separator comprising
       an inlet pre-connected to the plasma collect tubing; and
       a first outlet connected to the plasma protein collection container to connect the second hollow fiber membrane separator between the first outlet of the first hollow fiber membrane separator and the plasma protein collection container wherein separated plasma exiting the first hollow fiber membrane separator from the first membrane first outlet passes through the collect tubing to the second hollow fiber membrane separator for separation into desired plasma proteins and wherein such plasma proteins are collected in the plasma protein collection container;
    wherein the set further comprises a cassette having internal passageways for fluidly connecting the first membrane separator to the second membrane separator.

2. The disposable set of claim 1 further comprising a second outlet on the first membrane separator, and return tubing for returning the other blood components to a donor through the second outlet.

3. The disposable set of claim 2 further comprising a blood removal and return assembly for removing blood from a donor and providing it to the first membrane separator and fluidly connected to the return tubing for returning the other components back to the donor.

4. The disposable set of claim 3 further comprising a second outlet on the second membrane separator, and a plasma return assembly fluidly connected to the second outlet to return any uncollected plasma or plasma proteins back to a donor through the second membrane second outlet and the blood removal and return assembly.

5. The disposable set of claim 1 wherein the first hollow fiber membrane separator comprises a pore size for permitting plasma to pass through the membrane but not other blood components.

6. The disposable set of claim 5 wherein the second membrane separator comprises a membrane having a pore size for permitting plasma to pass through the membrane but not desired plasma proteins to be collected.

7. The disposable set of claim 6 wherein the pore size of the second membrane separator is such that low molecular weight plasma proteins pass through the membrane and high weight plasma proteins are collected.

8. The disposable set of claim 1 wherein the second membrane separator comprises a membrane having a pore size for permitting plasma to pass through the membrane but not desired plasma proteins to be collected.

9. The disposable set of claim 8 wherein the pore size of the second membrane separator is such that low molecular weight plasma proteins pass through the membrane and high weight plasma proteins are collected.

10. The disposable set of claim 1 further comprising
a second outlet on the second membrane separator, and
a plasma return assembly fluidly connected to the second outlet to return any uncollected plasma or plasma proteins back to a donor through the second membrane second outlet.

11. Apparatus for separating whole blood into plasma proteins comprising
a pump system for cooperating with an integrated pre-connected disposable set comprising
a removal pump for removing blood from a donor;
a return pump for returning uncollected whole blood components to the donor;
a collect pump for pumping separated plasma to a second hollow fiber membrane separator;
a integrated pre-connected set comprising
a first hollow fiber membrane separator for receiving blood removed by the removal pump and separating such blood into plasma and uncollected blood components;
a second hollow fiber membrane separator for receiving separated plasma pumped by the collect pump from the first membrane separator and for separating such plasma into at least one plasma protein fraction;
a collection container connected to the second hollow fiber membrane separator for receiving the at least one plasma protein fraction wherein the second hollow fiber membrane separator is between the first hollow fiber membrane separator and the collection container;
wherein the integrated pre-connected set comprises a cassette having a removal fluid flow passageway through which whole blood flows to the first membrane separator.

12. The apparatus of claim 11 further comprising a plasma return pump for returning any plasma or plasma proteins not collected from the second membrane separator to the donor.

13. The apparatus of claim 11 wherein the cassette further comprises a return fluid flow passageway through which uncollected blood components and return plasma flow to be returned to the donor.

14. The apparatus of claim 13 wherein the return fluid flow passageway comprises a reservoir for receiving uncollected plasma and blood components for return to the donor.

15. The apparatus of claim 11 wherein the cassette comprises a collect fluid flow passageway through which separated plasma flows from the first membrane separator to the second membrane separator.

16. The apparatus of claim 11 wherein the first membrane separator comprises a hollow fiber membrane with pore size for permitting plasma to pass through the membrane but not the uncollected whole blood components.

17. The apparatus of claim 16 wherein the second membrane separator comprises a membrane having a pore size for permitting plasma to pass through the membrane but not the at least one plasma protein fraction.

18. The apparatus of claim 17 wherein the pore size of the membrane of the second membrane separator is such that low molecular weight plasma proteins pass through the membrane and high weight plasma proteins form the plasma protein fraction to be collected.

19. The apparatus of claim 11 wherein the second membrane separator comprises a hollow fiber membrane having a pore size for permitting plasma to pass through the membrane but not the at least one plasma protein fraction.

20. The apparatus of claim 19 wherein the pore size of the membrane of the second membrane separator is such that low molecular weight plasma proteins pass through the membrane and high weight plasma proteins form the plasma protein fraction to be collected.

21. The method of collecting a concentrated plasma product from whole blood comprising:
removing whole blood from a donor;
separating the whole blood using a first hollow fiber membrane separator into a plasma component and other components;
returning the other components to the donor;
separating the separated plasma using a second hollow fiber membrane separator into at least one protein fraction;
collecting the separated at least one protein fraction; and
concentrating the collected at least one protein fraction using a plasma fractionator to further concentrate the desired proteins in the at least one fraction wherein the step of concentrating the collected at least one protein fraction comprises precipitating out the desired proteins using cold alcohol fractionation.

22. The method of collecting a concentrated plasma product from whole blood comprising:
removing whole blood from a donor;
separating the whole blood using a first hollow fiber membrane separator into a plasma component and other components;
returning the other components to the donor;
separating the separated plasma using a second hollow fiber membrane separator into at least one protein fraction;
collecting the separated at least one protein fraction; and
concentrating the collected at least one protein fraction using a plasma fractionator to further concentrate the desired proteins in the at least one fraction wherein the step of concentrating the collected at least one protein fraction comprises precipitating out the desired proteins using cold alcohol fractionation and passing the collected fraction through a stationary phase to concentrate the desired plasma proteins.

* * * * *